United States Patent [19]

Spaven et al.

[11] 4,235,232
[45] Nov. 25, 1980

[54] HUB DEVICE FOR PREVENTING LIQUID LEAKAGE

[75] Inventors: George D. Spaven, South Plainfield; Joseph J. Thomas; Howard Beroff, both of Bridgewater, all of

[73] Assignee: Johnson & Johnson, New Brunswick, N.J.

[21] Appl. No.: 936,267

[22] Filed: Aug. 22, 1978

[51] Int. Cl.³ .............................................. A61M 25/02
[52] U.S. Cl. ............................... 128/214.4; 128/349 R; 128/DIG. 16
[58] Field of Search ............. 128/214.4, 214.2, 214 R, 128/DIG.16, DIG. 26, 348, 349 R; 277/152, 207; 279/206 R; 251/6

[56] References Cited

U.S. PATENT DOCUMENTS

| | | | |
|---|---|---|---|
| 2,434,686 | 1/1948 | Clayton | 277/153 |
| 2,836,450 | 5/1958 | Riesing | 277/152 |
| 2,847,994 | 8/1958 | Huber | 128/214.2 |
| 3,825,001 | 7/1974 | Bennet et al. | 128/DIG. 16 X |
| 4,000,739 | 1/1977 | Stevens | 128/214.4 |
| 4,135,515 | 1/1979 | Muriot | 128/272 X |

Primary Examiner—Harry N. Haroian
Attorney, Agent, or Firm—Donal B. Tobin

[57] ABSTRACT

A hub device particularly suitable for use in a catheter placement unit which includes a catheter tube for insertion into a patient. The hub comprises a body with a passageway therethrough for the passage of the catheter tube. A resilient seal is associated with the passageway and is integrally formed on the body. This seal is adapted to permit the catheter tube to be slid into the passageway but is adapted to bear against the periphery of the tube to effect a seal around the tube. Thus, in use, liquid is prevented from leaking out of the hub.

2 Claims, 8 Drawing Figures

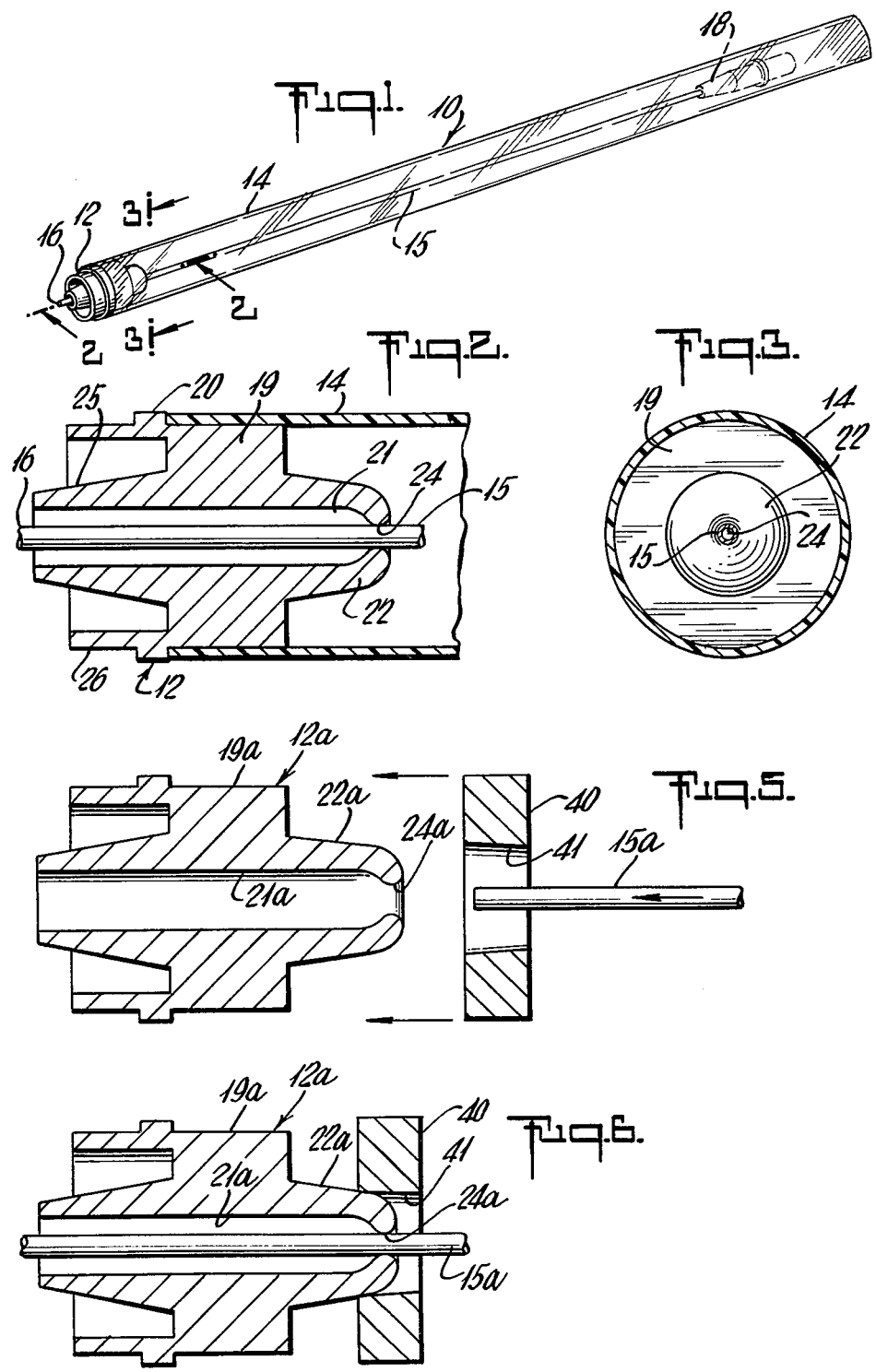

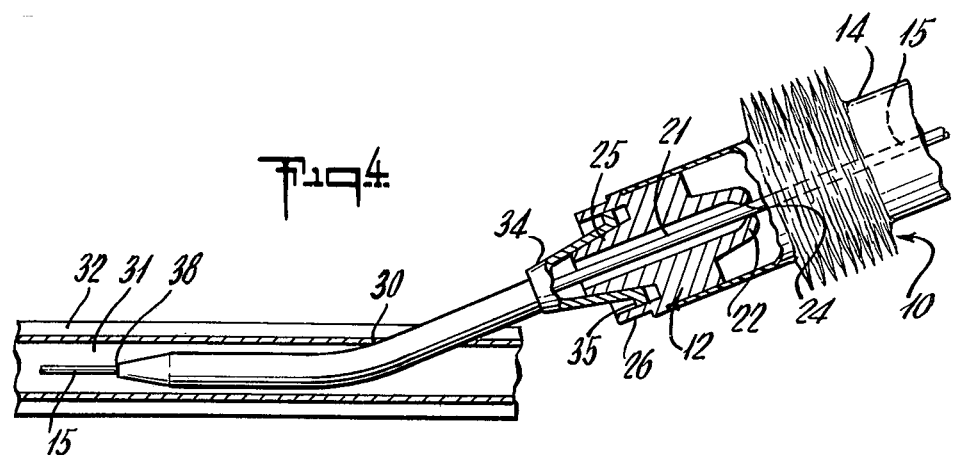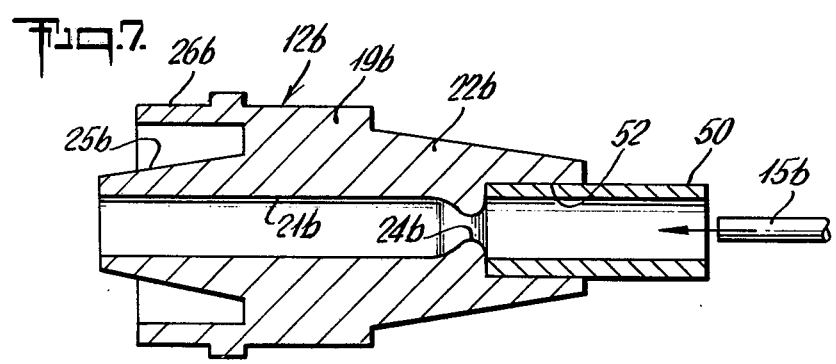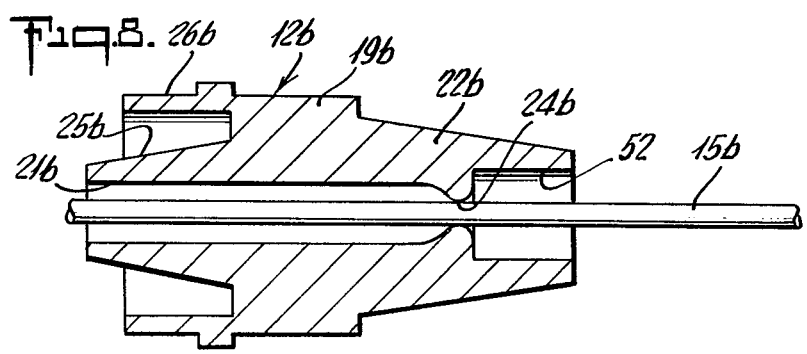

HUB DEVICE FOR PREVENTING LIQUID LEAKAGE

BACKGROUND OF THE INVENTION

The present invention relates to a hub device for preventing liquid leakage, and more particularly, concerns a hub suitable for use in a catheter placement unit which includes a catheter tube for insertion into a patient, the hub being particularly useful in preventing blood from leaking into the catheter placement unit.

Catheter placement units are employed for a variety of purposes, including the administration of liquids into the bloodstream, monitoring the central venous pressure and the like. A well-known and widely used technique for utilizing a catheter placement unit includes the use of an introducer catheter to which the catheter placement unit is connected; the catheter tubing from the placement unit is then slid through the introducer catheter and on into the vein or other body tissue of the patient. Although, in most cases, there is very little clearance between the outside surface of the catheter tubing and the inside surface of the introducer catheter wall, this clearance oftentimes causes problems.

For instance, inasmuch as both the introducer catheter and the catheter tubing of the catheter placement unit are both inserted into the vein of the patient during various medical procedures, the venous pressure may cause blood to rise into this clearance space between the two catheters. Once this happens, the blood may travel through this clearance space and eventually out of the connecting hub arrangement whereupon the blood then will leak onto the patient or surgical coverings. Some catheter placement units have recognized this problem and have successfully overcome this undesirable leakage. The catheter placement unit described in U.S. Pat. No. 3,825,001 includes an elastomeric diaphragm in the fitting of the catheter placement unit which tightly engages the outer periphery of the tubing. Thus, a seal is provided to prevent the leakage of blood between the catheter tubing and the introducer catheter. However, although the device described in this patent is functionally successful, the structure of the placement unit fitting is somewhat complicated and includes a number of components which may tend to add expense to the device.

Another catheter seal device is described in U.S. Pat. No. 3,970,089. This device includes an elastomeric member with a lumen therethrough, the elastomeric member located in a chamber inside a hollow rigid body. By distending the elastomeric member to constrict the lumen through which the catheter is passed, a seal is formed to prevent egress along the interface between catheter and the innermost surface of the elastomeric member. Various techniques of distending the elastomeric member are disclosed, including admitting air or other inflating fluid to a toroidal bladder which becomes progressively distended, and presses against the catheter to effect the seal. This type of sealing device is also somewhat complicated and lacks the simplicity of design, inexpense of manufacture and functional convenience in order to be compatible with the hub on a catheter placement unit. Accordingly, improvements in sealing the annular space between concentric catheter devices through which blood or other liquids may flow are still being sought. The present invention is directed to such improvements.

SUMMARY OF THE INVENTION

A hub device of the present invention comprises a body with a passageway therethrough for the passage of a tubular member through the body. Resilient sealing means is associated with the passageway and is integrally formed on the body. This sealing means is adapted to permit the tubular member to slide into the passageway but is also adapted to bear against the periphery of the tubular member to effect a seal around the tubular member.

In the preferred embodiment of this aspect of the invention, the hub is suitable for use in a catheter placement unit including a catheter tube. Both the body and resilient sealing means are integrally formed and are made from a flexible, elastomeric material.

Another aspect of the present invention is a catheter placement unit including a hub, a protective sleeve connected to the hub and a catheter tube within the sleeve adapted to pass through the hub for insertion into a patient. The hub is substantially as described above and in use, functions to prevent blood or other liquids from leaking out of the hub and into the sleeve.

From the structural standpoint, the hub device of the present invention is notably different from prior hub devices useful on catheter placement units or with concentric catheters which are placed into the bloodstream or other body liquids. For instance, the present hub is a one-piece device, i.e., the resilient seal and the body are integrally formed into a unitary structure. This offers the advantage of simplicity of structure, inexpense of manufacture and functional convenience. Moreover, the present hub device, in addition to providing an effective liquid seal, may also serve to lock the tubular catheter into position to prevent longitudinal movement of the catheter after the same has been inserted into position. Other advantages and benefits of the present invention are provided as well.

BRIEF DESCRIPTION OF THE DRAWINGS

FIG. 1 is a perspective view illustrating one embodiment of a catheter placement unit including a preferred hub of the present invention;

FIG. 2 is an enlarged cross-sectional view taken along line 2—2 of FIG. 1;

FIG. 3 is an enlarged cross-sectional view taken along line 3—3 of FIG. 1;

FIG. 4 is a view showing a patient and vein in section with an introducer catheter inserted in that vein, and showing a catheter placement unit, in fragmentary cross-section, connected to the introducer catheter with its catheter tubing fed through the introducer catheter and into the vein;

FIG. 5 is an alternate embodiment of the hub of FIG. 2 shown in enlarged cross-section and illustrated before assembly of the catheter tube into the hub;

FIG. 6 is an enlarged cross-sectional view of the embodiment of FIG. 5 with the catheter tube assembled in the hub;

FIG. 7 is another alternate embodiment of the hub of the present invention shown in enlarged cross-section before assembly of the catheter tube into the hub; and FIG. 8 illustrates the embodiment of FIG. 7 after the catheter tube is assembled in the hub.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated a catheter placement unit 10 which is utilized to deliver a catheter especially to a remote part of the human body. Catheter placement unit 10 is comprised of a hub 12, a protective sleeve 14 connected at one end to hub 12 and a catheter tube 15 within sleeve 14, the tube adapted to pass through hub 12 for eventual insertion into a patient. A distal end 16 of tube 15 is normally inserted in hub 12 so as to project a short distance from the hub thereby placing a catheter placement unit in a better state of readiness for utilization. At the proximal end of catheter tube 15 is a fitting 18 to which appropriate tubing from an administration set or a pressure monitoring device is connected after the catheter tube has been positioned. Sleeve 14 is preferably very pliant or flexible, and removable from the catheter placement unit after catheter tube 15 has been positioned in the patient.

Turning to FIGS. 2 and 3, hub 12 is more clearly illustrated. As can be seen in the drawings, hub 12 includes a generally cylindrically shaped body 19. On the periphery of body 19 is an annular shoulder 20 against which sleeve 14 lies and which assists in the connection of sleeve 14 to hub 12. A substantially circular passageway 21 extends through the longitudinal direction of body 19. One end of body 19 includes a tapered annular projection 22 around passageway 21. At the end of projection 22 is an annular dimple 24, the diameter of dimple 24 being less than the diameter of passageway 21. Dimple 24 thus forms a circular opening generally smaller than the diameter of catheter tube 15 before the latter is inserted into hub 12. As can be seen especially in FIG. 2, tube 15 has been inserted into passageway 21 of the hub; tapered projection 22 is designed to resiliently flex generally in a radially outward direction under the influence of catheter tube 15 being inserted through the circular opening formed by annular dimple 24. Both the relatively thin wall of the tapered projection and the fact that the body material is preferably flexible contribute to the resiliency of the tapered projection and allow catheter tube to be slid relatively easily into passageway 21. At the same time, however, annular dimple 24 bears against the periphery of catheter tube 15 to thereby form a seal between annular dimple 24 and tube 15. This seal is especially effective when body 19 and integrally formed projection 22 are made of a flexible, preferably elastomeric, material, such as natural rubber, synthetic rubber and the like.

At the opposite end of body 19 is a second tapered portion 25 serving as a male connector as will hereinafter be described. Tapered male connector 25 is preferably integrally formed on body 19 and extends substantially axially therefrom and is substantially concentric with passageway 21. It is noted that distal end 16 of the catheter tube extends a short distance from the end of tapered male portion 25; this is to assure that the catheter tube has been properly inserted into passageway 21 so that the operator of the catheter placement unit does not have to make such insertion while he is trying to connect the catheter placement unit to the introducer catheter. Surrounding tapered male portion 25 is an annular flange 26 which, together with tapered male portion 25, serves to lock the hub into a compatible female fitting on the introducer catheter. Although not shown for clarity sake, flange 26 may have threads or notches therein in order to provide a liquid-tight lock between hub 12 and the introducer catheter so that no blood or other liquids may leak from the connection. Such an arrangement is more clearly seen in FIG. 4, which also illustrates the use of the catheter placement unit and the advantageous features of the preferred hub of the present invention.

As can be seen in FIG. 4, an introducer catheter 30 has been inserted into a vein 31 of patient 32. The flexible nature of introducer catheter 30 assists in properly positioning the same in vein 31, while also minimizing any traumatic effects. Similarly, tubing 15 is also flexible for the same reasons. At the proximal end of introducer catheter 30 is a fitting 34 with an internal tapered surface which serves as a female connector. A flange 35 on fitting 34 assists in locking the hub of the catheter placement unit to the introducer catheter. The connection of the catheter placement unit 10 is made by the insertion of tapered male portion 25 into fitting 34, with flange 26 on the hub and flange 35 on the fitting cooperating to provide a liquid-tight lock. Catheter tube 15 is then manipulated while still enclosed by protector sleeve 14 into introducer catheter 30 and then into vein 31 of the patient. At the distal end 38 of introducer catheter 30 it is oftentimes difficult to provide a tight seal between the emerging catheter tube and the introducer catheter. In this condition, the venous pressure may cause blood to enter the annular space between the catheter tube and the inside wall of the introducer catheter. Blood may then travel up through the introducer catheter and the connection between fitting 34 and hub 12 and enter into passageway 21 in the hub. With no seal provided, it can be seen that blood would then deposit into sleeve 14, or if the sleeve had been removed, would deposit on the patient. However, the present hub device overcomes this eventuality by the seal provided by resilient projection 22 and annular dimple 24 which bears tightly against the periphery of catheter tube 15. Accordingly, any blood which may travel up into passageway 21 will be blocked and prevented from escaping from the hub.

Referring to FIGS. 5 and 6 an alternate embodiment of the previously described preferred hub is illustrated, with most of the features of the alternate hub being the same as the former embodiment; thus, the same base reference numerals are used for corresponding components. In this alternate embodiment, a compression ring 40 is utilized in conjunction with tapered projection 22a to not only provide an effective seal between annular dimple 24a and catheter tube 15a, but also to assure that catheter tube 15a is locked into position. This is accomplished by providing ring 40 with a hole 41 which will fit over the narrow tapered portion of projection 22a. As seen in FIG. 6, after catheter tube 15a has been inserted into passageway 21a and is properly positioned in the vein or other body tissue of the patient, it is often desirable to fix the catheter tube in place so that it can no longer move longitudinally. This desirable feature is accomplished by sliding ring 40 onto tapered projection 22a which thereby causes increased compression of annular dimple 24 against catheter tube 15a. As the compression force increases so does the friction force between the two components so that sliding of catheter tube 15a becomes more difficult. In this regard, an effective lock is created so that catheter tube 15a is prevented from moving longitudinally. Thus, the tip of catheter tube 15a is maintained in the desirable remote position inside the body especially when using this embodiment of the catheter placement unit hub device.

Another alternate embodiment of the preferred hub device is illustrated in FIGS. 7 and 8, this alternate embodiment also being, in most respects, similar to the first described embodiment. However, instead of a compression ring as utilized with the previous embodiment, this second alternate embodiment employs a tension ring 50 in order to assist in the locking of the catheter tube in position. It is noted that tapered portion 22b is formed with a somewhat thicker wall than in the previous embodiments. This, accordingly, reduces the resiliency of this projection and tends to make it more difficult to flex annular dimple 24b. Annular dimple 24b, in this embodiment, is recessed inwardly a short distance from the end of the hub body. A counterbore 52 or like recess is formed in projection 22 between annular dimple 24b and the end of body 19b. Before and during insertion of catheter tube 15b through hub 12b and into the patient, tension ring 50 is inserted into bore 52; tension ring 50 is a substantially concentric tube in which its outside diameter not only fits into bore 52 but urges projection 22b in a radially outward direction and it thus maintains the same under tension while the catheter tube is being slid into position. With tension ring 50 in position, annular dimple 24b is sufficiently opened up to allow catheter tube 15b to smoothly slide through hub 12b and into its proper position into the patient. Once catheter tube 15b is in its proper position, as illustrated in FIG. 8, tension ring 50 is removed from bore 52. As alluded to above, the stronger walls of projection 22b react in a radially inward direction following removal of the tension force. As a result, a tight seal is formed by annular dimple 24b around catheter tube 15b which is sufficient to lock the tube in place to substantially prevent its longitudinal movement.

Thus, the present invention provides a hub which is especially suitable for use in a catheter placement unit, and which prevents liquid leakage therefrom.

What is claimed is:

1. A hub suitable for use in a catheter placement unit, which includes a catheter tube comprising:

an annular, flexible body having a passageway therethrough for the passage of said catheter tube through said body;

an annular flange extending coaxially from said body about said passageway and defining a coaxial extension for said passageway;

an annular dimple on the free end of said flange projecting into and restricting said passageway and providing free sliding, sealable engagement with the periphery of said tube;

the outer wall of said flange tapering toward the axis of said passageway from said body to said dimple; and, a generally annular, rigid compression ring adapted to slide over said flange and compress said dimple against said catheter tube to lock and seal said catheter tube in place in said body; the interior wall of said ring being cooperatively tapered for engagement with said tapered flange wall;

said tapering outer wall of said flange providing a flexible, thin wall portion of said flange in the vicinity of said dimple to facilitate the compression of said dimple about said catheter tube.

2. A hub suitable for use in a catheter placement unit, which includes a catheter tube comprising:

an annular, flexible body with a passageway therethrough for the passage of said catheter tube through said body;

an annular flange extending coaxially from said body about said passageway and defining a coaxial extension for said passageway;

an annular dimple recessed from the free end of said flange and projecting into and restricting said passageway to lockingly and sealingly engage the periphery of said catheter tube in said body;

a portion of said passageway, from said recessed dimple to the free end of said flange, having an increased diameter;

an annular tension ring having an outer diameter greater than said increased diameter portion of said flange and adapted for insertion into said increased diameter portion to expand the restriction in said passageway provided by said recessed dimple to provide free sliding and sealable engagement between said dimple and said catheter tube while said tension ring is in place;

the outer wall of said flange tapering toward the axis of said passageway, from said body to said dimple, to provide a flexible, thin wall portion of said flange in the vicinity of said expanded diameter portion to facilitate the expansion of said dimple restriction when said tension ring is inserted.

* * * * *